United States Patent [19]
Nugent

[11] Patent Number: 5,143,626
[45] Date of Patent: Sep. 1, 1992

[54] SLUDGE DEHYDRATER HAVING SPECIALLY DESIGNED AUGERS AND INFRARED HEATER ELEMENTS

[75] Inventor: James E. Nugent, Lafayette, La.

[73] Assignee: Sludge Drying Systems, Inc., Breaux Bridge, La.

[21] Appl. No.: 552,784

[22] Filed: Jul. 10, 1990

[51] Int. Cl.⁵ .................. B01D 1/00; F24C 15/24
[52] U.S. Cl. ........................ 210/748; 34/31; 34/180; 210/149; 210/179; 210/770; 366/323; 432/24; 432/31
[58] Field of Search ............ 34/17, 27, 28, 39, 40, 34/46, 60, 68, 73–76, 180, 181, 128, 182, 31; 210/85, 179, 180, 243, 742, 770, 748, 609, 149; 110/224; 219/388, 389; 432/107, 108, 24, 31, 49; 366/88, 323, 326

[56] References Cited

U.S. PATENT DOCUMENTS

| | | | |
|---|---|---|---|
| 3,744,145 | 7/1973 | Maxwell et al. | 34/180 |
| 4,050,900 | 9/1977 | Hobbs et al. | 34/39 |
| 4,330,946 | 5/1982 | Courneya | 34/17 |
| 4,380,496 | 4/1983 | Maffet | 210/609 |
| 4,882,851 | 11/1989 | Wennerstrum et al. | 34/60 |
| 4,939,346 | 7/1990 | Bailey et al. | 34/128 |
| 4,993,943 | 2/1991 | Norris et al. | 110/224 |
| 5,052,858 | 10/1991 | Crosby et al. | 432/108 |

Primary Examiner—Robert A. Dawson
Assistant Examiner—Joseph Drodge
Attorney, Agent, or Firm—William W. Stagg

[57] ABSTRACT

The invention discloses an apparatus and process for destroying pathogens and dehydrating streams of waste in one, continous process. More particularly, the invention contains an auger with specially modified, variably angled blades which agitates a stream of waste. Also, contained in tandem with the auger, a series of variably angled infrared radiate elements are positioned above the augar exposing the moving stream of waste to radiation. Thus, as the waste stream is transported along, the auger blades continually expose the waste stream to the radiation, thereby killing the entrapped pathogens and evaporating the insitu water. Further, the auger and infrared radiation heater elements are encased in a sealed trough, thus sealing in the heat being generated by this process. By sealing the trough, the heat provides excess energy to aid in destroying pathogens and evaporating the insitu water contained in the waste stream, until the water content is less than or equal to five per cent (5%) by unit volume.

10 Claims, 3 Drawing Sheets

SLUDGE DEHYDRATER HAVING SPECIALLY DESIGNED AUGERS AND INFRARED HEATER ELEMENTS

BACKGROUND OF THE INVENTION

This invention relates to treatment of waste streams and more particularly to the use of infrared radiation along an auger's path to efficiently dehydrate and purify the waste stream.

Treatment of waste streams (such as muncicipal sludge, hazardous waste or sewage) posses a major problem for both government and civilian entities. One of the major obstacles is that the waste contains pathogens; a second, the waste by its nature, contains an insitu amount of water. Thus, because pathogens are inherently dangerous, the waste must be purified before the waste is disposed. Furthermore, because the waste must be disposed at landfills, the water takes up much needed space.

Therefore, a major problem encountered in this field relates to treating the municipal and industrial waste in an economical fashion in such a way that the inherent impurities are destroyed. A second major problem is presented when the waste, which esentially has been treated to destroy the impurities, is disposed at a landfill which has a finite amount of disposal area. Thus, considering the above problems, it is one of the objects of this invention to provide an apparatus and process which can effectively and economically destroy pathoganic organisms. Further, it is an object of this invention to provide for an apparatus and process which will efficiently and economically dehydrate the waste in order to reduce the amount of area required for disposal. Furthermore, it is an object of this invention to provide for an invention which allows for continuous treatment and dehydration of the waste stream, thereby allowing for twenty-four hour treatment and twenty-four hour output of the dehydrated, purified waste.

In the past, various methods and apparatuses have been utilized for the treatment and disposal of sewage. In U.S. Pat. No. 4,013,552 by Krauter, a process of sonobioaeration was revealed wherein ultrasonic energy and ultraviolet energy are utilized to sanitize micro-organizims. However, this process' primary focus is on the ultrasonic energy, and sonobioaeration does not even attempt to address the insitu water problem.

Also, in U.S Pat. No. 4,380,496 by Maffet a process to mechanically dewater municipal sledge was disclosed. In particular, this process employs an auger enclosed in a porous wall. However, this invention does not address the pathogen problem encountered in municipal waste, and further, the invention must utilize pressuration to a superatmospheric pressure in order for the process to work.

In U.S. Pat. No. 4,793,931 by Stevens, a process for treating liquid or solid waste containing an organic contaminant was disclosed. In this process, ultraviolet irradiation is performed; however, before the ultraviolet irradation, the waste must first be contacted with a perfloriated solvent in a batch type of treatment.

Other prior art which show the use of heat and/or a ultraviolet irradation can be found in U.S. Pat. No. 3,960,725 by Bjerno, et al; U.S. Pat. No. 3,666,106 by Green; and U.S. Pat. No. 4,906,387 by Pisani.

SUMMARY OF THE INVENTION

The sludge dehydrator provides for an efficient and economical total treatment of waste streams. First toxic pathogens, such as polio and colora virus, are destroyed. Second, the municipal waste is dehydrated, elimating the water content to less than five per cent (5%) per unit weight.

More particularly, the invention includes a type of auger with specially designed paddles, and infrared lamps positioned directly above the auger; moreover, the invention can be continued on one, movable skid unit. The auger, which is specially designed to contain modified paddles, is energized so that rotation of the blades can be controlled. The rotation of the auger and blades causes agitation of the sludge which in turn causes greater surface area of the waste stream to be exposed. Further, in designing the apparatus, the length of the auger is dependent on the quantity of waste being processed: the greater the stream of waste and moisture content, the longer the required design length.

The auger is encased in a metal bin, known as a conveyor trough, which will seal the contents from the outside atmosphere. Thus, once the infrared radiation begins, heat will be generated. However, the heat and gases produced will be trapped and recirculated within the enclosed auger.

The radiation is provided by means of an infrared radiation heater. The infrared radiate heaters are placed along the length of the auger and are positioned at differing angles to the auger. Thus, as agitation of the waste stream is caused by the auger, the previously unexposed surface of waste stream (being exposed by the auger) will be subjected to infrared radiation, thereby ensuring proper surface exposure. The heat generated by the radiation will destroy all known pathogens when the moisture content of the sludge is less than ten per cent (10%) and the temperature exceeds 80° C. for thirty (30) minutes, which is in compliance with the Environmental Protection Agency's regulation regarding processes to further reduce pathogens. See generally 40 CFR Part. 259, Appendix II.

A feature of this invention includes the auger with custom designed paddles. Therefore, the auger is designed to agitate and mix the sludge so that the differing surface area of the sludge is continually being exposed. Further, the auger rate of rotation can be varied by operator control. Thus, when dealing with greater quantities of sludge, the auger's rotation can be decreased, which will in turn cause the sludge to move slower, exposing greater surface area to the infrared radiation.

Still another feature of the invention includes being able to increase the design length of the auger for increasing quantities of the sludge. This produces the advantage of allowing the sludge to be agitated, with the sludge being exposed for the proper amount of time to the infrared radiation.

Yet another feature of the invention is the use of infrared radiation to generate heat and kill pathogens. Thus, in use of this invention, there is the advantage of having the sludge absorb infrared radiation. The radiation will not only kill pathogens, but the radiation will also generate heat causing water to evaporate. The heat is sealed inside the auger system, and is also a source which kills pathogens.

The power to the infrared radiate heaters can be varied; thus, the operator can control, depending on the stream of waste being processed, the amount of heat being generated, which is another advantage of this invention.

Also, a feature of the invention includes having the auger and infrared radiation functioning together and at the same time. Thus, this tandem relationship allows for the killing of pathogens and drying of the waste stream in one continuous operation. Put another way, the tandem relationship eliminates the need for one separate treatment porcess for the purifying of the waste, and then an independent treatment process for dehydrating the waste.

Finally, it should be understood that this apparatus and process applies to the treatment of any waste stream. For purposes of this invention, a waste stream includes any mixture of water and solids, which because of its nature, the water and solids are intermixed with either the water being entrapped in the solids or the solids being suspended in the fluid phase.

It should be noted that the terms waste stream and sludge will be used interchangeably in this specification.

DESCRIPTION OF THE PREFERRED EMBODIMENT

Figure 1:
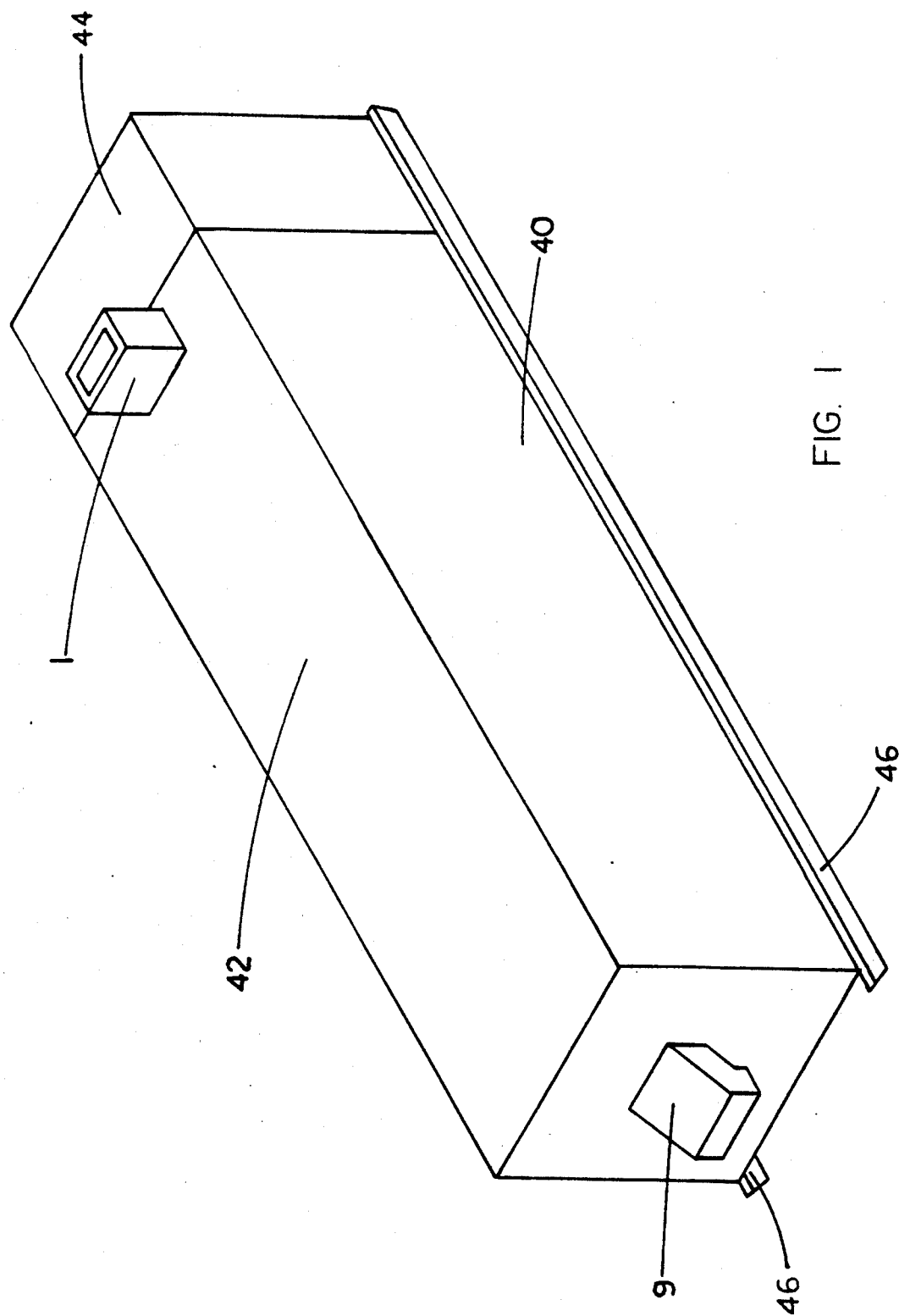
FIG. 1 is a perspective view of the invention mounted on skid unit.

Referring now to the drawings and more particularly to FIG. 1 there is shown a perspective view of the sludge dehydrater apparatus 40. The apparatus 40 is comprised of an outer sludge housing section 42 and a power and control section housing 44. The apparatus 40 is mounted to a skid unit generally designated 46. Sludge to be processed enters the apparatus 40 by means of an air tight hooper 1 and exits after processing by means of an exit chute 9.

Figure 2:
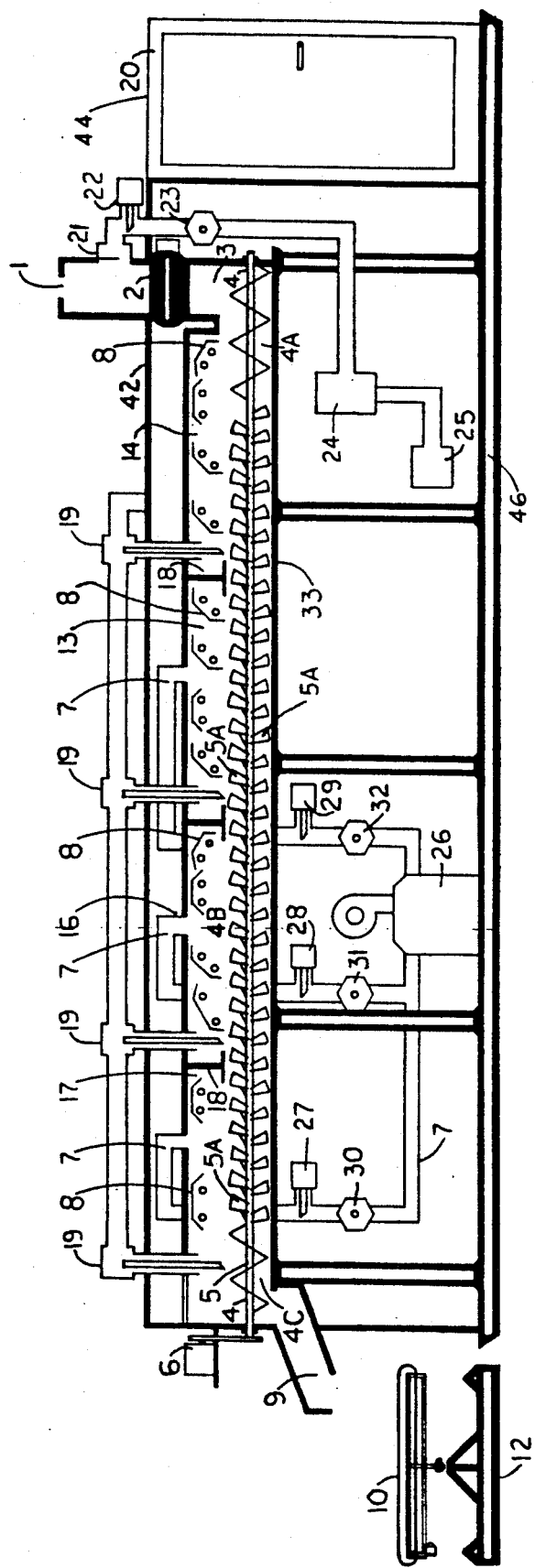
FIG. 2 is a longitudinal cross-sectional view of the invention showing the auger paddles and infrared heaters, mounted on a skid.

FIG. 2 is a longitudinal cross-sectional view of the sludge dehydrating apparatus 40 shown in FIG. 1. In the preferred embodiment, the sludge enters the apparatus 40 through the air tight hopper 1 where the sludge will fall onto a shredder 2 where the sludge is shredded into fine particles. The shredded sludge is allowed to funnel through a feed section 3 and onto the sludge conveyor trough 33. The sludge conveyor trough 33 is a metal bin running longitudinally through the apparatus 40 from the feed section 3 to the exit chute 9. Encased within the sludge conveyor trough 33 is a sludge conveying auger 4 that runs the length of the conveyor trough 33. The sludge conveying auger 4 is comprised of an elongated metal tube 5 to which is attached a first screw conveyor flight auger 4A at the feed section 3 end of the sludge conveyor trough 33, an intermediate auger section 4B having a plurality of variably pitched paddles 5A and a second screw conveyor flight auger section 4C at the exit chute 9 end of the sludge conveyor trough 33. The sludge conveying auger 4 is turned by means of a variable speed motor 6 attached to the metal tube 5 and mounted to the housing 42 of apparatus 40.

The sludge conveyor trough 33 is supported at intervals by steel supports 48 to provide rigid support of the conveyor trough 33. The trough 33 has a plurality of trough covers 50 to which a plurality of infrared radiation heaters 8 are attached. The heaters 8 are positioned at varying angles over the auger 4 as shown in FIG. 2 to ensure that the sludge, being agitated by the variable pitch paddles 5A of the auger 4 as the sludge moves along the conveyor trough 33, is fully exposed to the radiation.

At the point the sludge enters the sludge conveyor trough 33, the conveying auger 4 including the variable pitch mixing paddles 5A have been energized and are turning by means of the motor 6. The rotational speed of the auger 4 is determined at the option of the operator and dependent on the quality and quantity of the waste stream. Once the auger 4 has been energized the sludge is moved along the conveyor trough 33 from the first conveyor flight auger section 4A to the intermediate auger section 4B at which point the paddles 5A begin the agitation and mixing of the sludge. The sludge is continuously being mixed which causes greater surface area of the sludge to become exposed to the radiation generated by the infrared heaters. As the sludge is transported along the route of the conveyor trough 33 by means of further rotation of the auger 4, the sludge is dried by the irradiation from the infrared heaters 8 located above the auger 4 along the path of the sludge conveyor trough 33. As the dried sludge nears the exit chute 9, the second conveyor flight auger section 4C conveys the dried sludge to the exit chute 9 where the sludge is dumped onto a discharge conveyor 10 or other means to move the dried sludge away from the apparatus 40. The discharge conveyor 10 is mounted on a frame 12 that can be positioned at any desired location for loading of the dried sludge onto trucks or sludge boxes.

In the preferred embodiment, the conveyor trough 33 is divided into four heating zones generally designated 14, 15, 16 and 17. Each heating zone has a plurality of infrared radiation heaters 8 where infrared radiation can be applied to the sludge as it is moved along the path of the conveyor 33 by means of the auger 4. Each heating zone is capable of applying infrared radiation of variable intensity, at the option of the operator. The heating zones are separated from each other by means of a partition 18.

The temperature in each heating zone is sensed by a thermocouple 19. A temperature set-point control is incorporated in the power and control panelboard 20 for setting the desired temperature in each heating zone.

While the heat which is generated by the infrared heater is contained in the conveyor trough 33, the steam generated from the evaporation of water from the sludge within the conveyor trough 33 is evacuated by means of an exhaust fan 21 located at the sludge inlent hopper 1 into an exhaust fan duct 23. The temperature of the steam vapors being removed is sensed by a thermocouple 22 mounted within the exhaust fan duct 23 which has a set point control incorporated in the power and control panelboard 20 to control an exhaust duct control valve 23A within the exhaust duct 23 by means of an SCR drive to moderate the control valve 23A to allow for increased or decreased steam vapors at a preselected temperature.

The steam removed by the exhaust fan 21 into the exhaust fan duct 23 will enter a condensor 24 for further condensing and then later for complete discharge of the steam from the apparatus 40 by means of a water operated eductor 25 connected by duct work to the condensor 24. The excess steam, vapors and condensate drawn by the exhaust fan 21 from the sludge conveyor 33 to the condensor 24 and then to the eductor 25 is mixed with a stream of water in the throat of the eductor 25 and the entire fluid mixture is discharged and transported back to a treatment facility.

A hot air process heater 26 is installed within the apparatus 40 to provide and maintain a constant ambient temperature within the conveyor trough 33. The purpose of the hot air process heater 26 is to maintain a minimum temperature. Hot air is delivered to three heating zones 15, 16, and 17 of the conveyor trough 33 through a series of hot air ducts 7 where thermocouple 27, 28 and 29 are installed for temperature regulation. The velocity of hot air is measured by velocity meters 30, 31 and 32 transmitted to the electric control panel where the velocity of hot air to each zone is regulated.

The entire apparatus 40 is contained in a housing designated 42 and 44 and is constructed of steel plates or other suitable structural material and the apparatus 40 is constructed on a skid 46 so that the apparatus 40 can be transported from one location to another.

In the preferred embodiment the total length of the auger 4 is 40 feet. At this length, and as mentioned previously, the conveyor trough 33 containing the auger 4 will be separated into four heat zones designated 14, 15, 16 and 17. Each heat zone has four 480 volt, 3 phase, 60 Hertz #7 infrared heaters designated 8 situated at various angles to the auger 4.

In the preferred embodiment, when the desired processing time for a quantity of sludge having a water content of 80% per unit weight is one hour, the rate of rotation of auger 4 will be approximately 20 revolutions per minute with the heaters 8 set at 500° F. The processed sludge output will be 1600 pounds an hour and the ambient temperature in the conveyor trough will be approximately 450° F.

Figure 3:
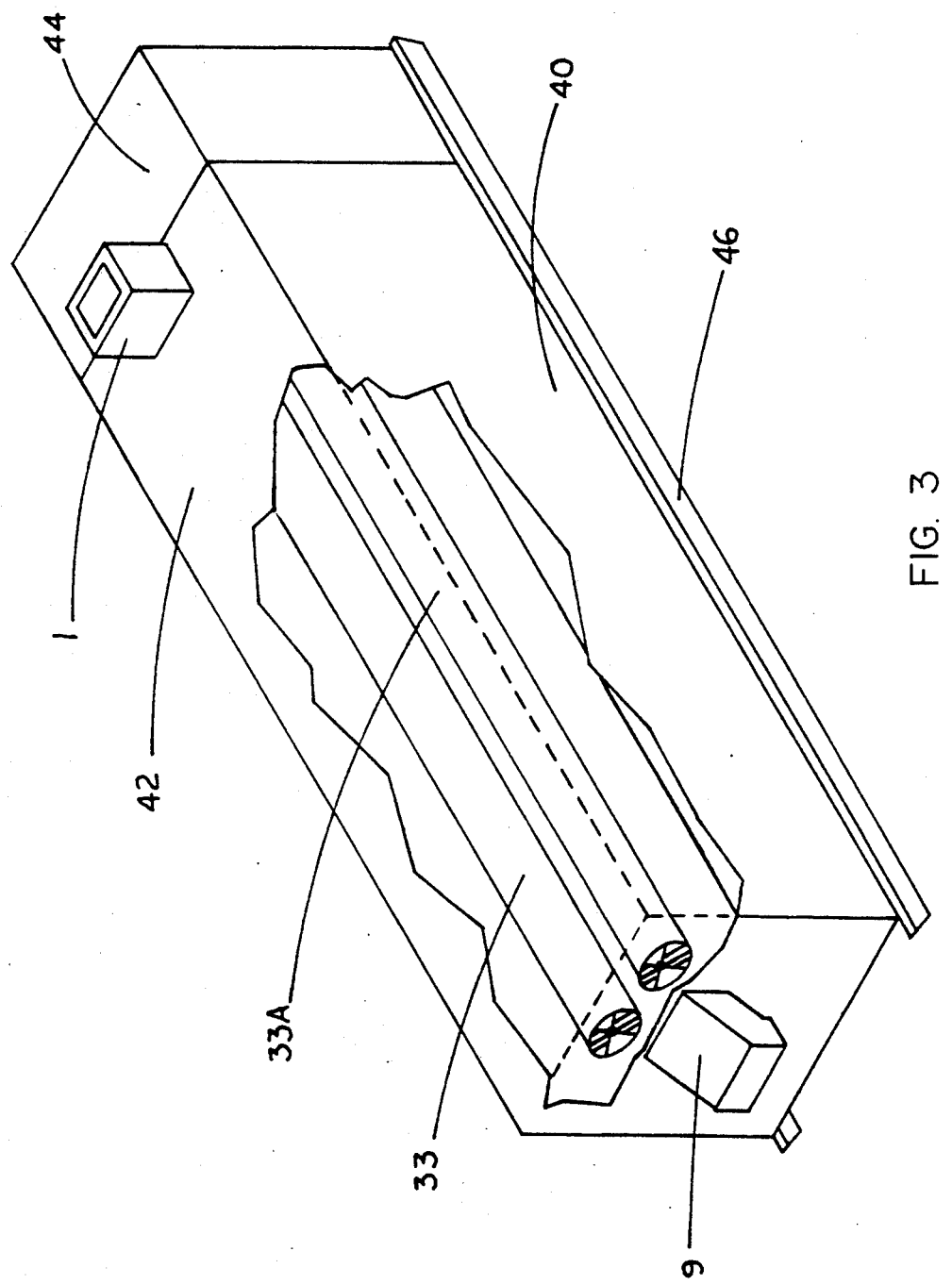
FIG. 3 is a broken line perspective view of the invention showing a series of conveyors or troughs, having the auger, paddles, and infrared heaters.

Referring to FIG. 3, it should be understood that if one wanted to double the processed sludge output, the apparatus 40 can be simply modified by laying a second conveyor trough 33A next to the original conveyor trough 33 with accompanying infrared heaters 8. Furthermore, it should also be noted that for a given processing time and quality of sludge the desired length of the auger 4 with the accompanying infrared heaters 8 is dependent on the rate of sludge input. Therefore, it is possible, that if one increases the length of the auger 4, and the number of overhead infrared heaters 8, the volume of sludge which can be processed may be increased. Likewise, if the length of the auger 4 is shortened and the number of infrared heaters 8 reduced, it would necessarily decrease the volume of the sludge output. Thus, the capacity for processed sludge output of the apparatus 40 is directly proportional to the length of the auger 4 and the number of associated heaters 8 positioned above the auger 4 for a given processing time and sludge type. The processing time is directly related to the rotational speed of the auger 4 which can be varied by the operator.

While the above preferred embodiments of the process have been described, it will be understood that changes and variations can be made without departing from the spirit and scope of the invention, as defined in the following claims.

I claim:

1. An apparatus for treating a waste stream, comprising:

(a) An enclosed conveyor trough, said conveyor trough having a first end and a second end;
(b) An auger having a longitudinal shaft and a plurality of variably positioned paddles mounted along said shaft said auger being positioned within said conveyor trough;
(c) A plurality of heating zones along said conveyor trough, said zones being separated from each other by a partition, each of said zones having a plurality of infrared heating elements variably angled within said conveyor trough;
(d) Means for introducing hot air into said heating zones to maintain selected, respective ambient temperatures.
(e) Means for introducing said waste stream at said first end of said conveyor trough;
(f) Means for turning said auger so as to move and mix said waste stream along the path of said conveyor trough; and
(g) Outlet means for removing said waste stream from said second end of said conveyor trough.

2. An apparatus for treating a waste stream, comprising:

(a) A plurality of augers, each auger having a first screw section, an intermediate section having a plurality of variably pitched paddles, and a second screw section;
(b) A plurality of Longitudinal conveyor troughs, each of said troughs having one of said augers placed longitudinally within said trough;
(c) Means for covering and sealing said troughs;
(d) A plurality of infrared heating elements mounted at various angles above each of said augers and within each of said troughs;
(e) Means for injecting said waste stream into each of said troughs at the first screw section of each of said augers;
(f) Means for turning each of said augers so as to move said waste stream along said augers within said troughs from said first screw auger sections to said intermediate paddle sections and finally to said second screw auger sections for mixing and exposing said waste stream to said heating elements; and
(g) Means for discharging said waste stream from said troughs.

3. A process for treating a waste stream, comprising the steps of;

(a) Providing a continuous waste stream to a plurality of enclosed longitudinal conveyor troughs;
(b) Heating the paths of said troughs by means of a plurality of variably angled infrared heating elements located within said troughs;
(c) Transporting and mixing said waste stream along the paths said conveyor troughs by means of a rotating auger in each of said troughs, each of said augers having a plurality of variably pitched paddles; and
(d) Ejecting said treated waste stream from said troughs.

4. A process for treating a waste stream as recited in claim 3 wherein said waste stream is sewage sludge.

5. An apparatus for dehydrating sludge, comprising;

(a) a conveyor trough having a longitudinal axis;
(b) an auger positioned within and along said longitudinal axis of said trough, said auger having a plurality of variably pitched paddles;
(c) means for transporting said sludge into said trough;

(d) means for generating infrared heat within said trough said means for generating comprising elements being mounted at varying angles;
(e) means for turning said auger so as to move said sludge along said trough so as to expose said sludge to said infrared heat for drying of said sludge;
(f) means for removing said dehydrated sludge from said trough.

6. An apparatus for treating a waste stream, as recited in claim 5, further comprising:
(a) Means for generating hot air; and
(b) Means for transporting said hot air to and from said conveyor trough to maintain a selected ambient temperature within said conveyor trough.

7. An apparatus for dehydrating and purifying a waste stream as recited in claim 5, wherein said means for generating infrared heat within said trough includes a plurality of infrared heating elements mounted to said trough at various angles above said augers.

8. An apparatus for dehydrating and purifying a waste stream, comprising:
(a) a longitudinal conveyor trough;
(b) an auger positioned longitudinally within said trough, said auger having a plurality of variably pitched paddles;
(c) means for placing said waste stream into said conveyor trough;
(d) means for generating infrared heat within said trough said means for generating comprising elements being mounted at varying angles;
(e) means for convering said trough;
(f) means for turning said auger so as to move said waste stream along said trough so as to expose said waste stream to said infrared heat for dehydrating and purifying said waste stream; and
(g) means for removing said dehydrated and purified sludge from said trough.

9. An apparatus for dehydrating and purifying a waste stream as recited in claim 8, wherein said means for generating infrared heat within said trough includes a plurality of infrared heating elements mounted to said trough at various angles above said augers.

10. A apparatus for treating a waste stream as recited in either or of claim 8 wherein said apparatus is adapted for treatment of sewage sludge.

* * * * *